| United States Patent [19] | [11] Patent Number: 4,729,956 |
|---|---|
| Hopkins | [45] Date of Patent: Mar. 8, 1988 |

[54] STABILIZED ALCOHOL OXIDASE COMPOSITIONS AND METHOD FOR PRODUCING SAME

[75] Inventor: Thomas R. Hopkins, Bartlesville, Okla.

[73] Assignee: Phillips Petroleum Company, Bartlesville, Okla.

[21] Appl. No.: 857,862

[22] Filed: May 1, 1986

[51] Int. Cl.$^4$ .......................... C12N 9/96; C12N 9/04; C12Q 1/26

[52] U.S. Cl. ........................ 435/188; 435/25; 435/28; 435/190; 435/27

[58] Field of Search .................. 435/188, 25, 28, 190

[56] References Cited

U.S. PATENT DOCUMENTS

| 3,598,704 | 8/1971 | Dahlqvist | 195/103.5 |
|---|---|---|---|
| 3,945,889 | 3/1976 | Mima et al. | 195/62 |
| 3,974,036 | 8/1976 | Snell | 195/65 |
| 4,080,262 | 3/1978 | Beaucamp | 195/63 |
| 4,121,905 | 10/1978 | Maurukas | 23/230 B |
| 4,271,264 | 6/1981 | Modrovich | 435/14 |
| 4,273,868 | 6/1981 | Walter | 435/14 |
| 4,414,334 | 11/1983 | Hitzman | 435/190 |
| 4,430,427 | 2/1984 | Hopkins | 435/25 |
| 4,450,153 | 5/1984 | Hopkins | 424/94 |
| 4,543,326 | 9/1985 | Miyashita et al. | 435/15 |
| 4,619,898 | 10/1986 | Hopkins | 435/190 |
| 4,642,286 | 2/1987 | Moldowan | 435/25 |

FOREIGN PATENT DOCUMENTS 133481 2/1985 European Pat. Off. .

*Primary Examiner*—Lionel M. Shapiro
*Attorney, Agent, or Firm*—J. E. Phillips

[57] ABSTRACT

Alcohol oxidase is rendered storage stable in dried form by the addition thereto of small amounts of at least one of peroxidase, catalase, hemoglobin, cytochrome c and myoglobin.

16 Claims, No Drawings

4,729,956

STABILIZED ALCOHOL OXIDASE COMPOSITIONS AND METHOD FOR PRODUCING SAME

This invention relates to enzymes. In one aspect, this invention relates to the preservation of the activity of enzyme compositions during drying, handling and storage. In yet another aspect, this invention relates to novel enzyme compositions which are stable in dry form to exposure to air and/or elevated temperatures.

BACKGROUND

The enzyme alcohol oxidase is capable of promoting a large number of enzymatic conversions, e.g. the oxidation of primary alcohols to aldehydes. Due to the ready availability of alcohol oxidase and the essentially stoichiometric nature of the conversions promoted by alcohol oxidase, the enzyme has come into increased usage for analytical purposes. However, one problem encountered when using alcohol oxidase in some analytical procedures is the loss of enzyme activity when the enzyme is subjected to a variety of storage and/or handling conditions. Such loss in enzyme activity increases the amount of enzyme required for a given application and reduces the reliability of the analysis in which the enzyme is employed.

Frequently, it is desired to store substantial quantities of alcohol oxidase in order to facilitate carrying out numerous analytical procedures. A convenient form in which to store desired quantities of alcohol oxidase would be to provide the alcohol oxidase as a dry powder or film. Unfortunately, it is commonly observed that the enzyme activity of alcohol oxidase stored as a dry powder or film is reduced substantially with time. In addition, the actual process of forming such dry powder or film, i.e., by removing water from an alcohol oxidase solution, can also cause substantial losses in enzyme activity.

OBJECTS OF THE INVENTION

It is, therefore, an object of the present invention to provide essentially dry compositions containing alcohol oxidase which are stable to prolonged exposure to air and/or elevated temperatures.

It is another object of the present invention to provide a process for drying aqueous solutions of alcohol oxidase without significantly reducing the enzyme activity of the alcohol oxidase.

These and other objects of the invention will become apparent from the disclosure and claims herein provided.

STATEMENT OF THE INVENTION

I have discovered that stable, essentially dry alcohol oxidase compositions result when stabilizing amounts of at least one stabilizing agent selected from the group consisting of peroxidase, catalase, hemoglobin, cytochrome c, and myoglobin, are admixed with essentially dry alcohol oxidase; or when at least one of the above stabilizing agents is added to an aqueous alcohol oxidase containing solution prior to removing the major portion of water from the alcohol oxidase solution.

DETAILED DESCRIPTION OF THE INVENTION

In accordance with the present invention, novel enzyme compositions are provided consisting essentially of alcohol oxidase and a stabilizing amount of a stabilizing agent selected from the group consisting of peroxidase, catalase, hemoglobin, cytochrome c and myoglobin.

In accordance with another embodiment of the invention, a method for preparing stable, essentially water-free alcohol oxidase containing compositions is provided which comprises suspending up to 100 mg/mL of alcohol oxidase in aqueous medium in the presence of a stabilizing amount of at least one stabilizing agent selected from the group consisting of peroxidase, catalase, hemoglobin, cytochrome c and myoglobin; then subjecting the alcohol oxidase containing suspension to conditions suitable to produce an essentially dry alcohol oxidase preparation.

The term "essentially dry" as used in this specification refers to compositions with substantially all free, unbound water removed, but does not reflect on the amount of water which may remain bound to the enzymes being dried. Such enzyme bound water can amount to as much as 5–10 weight percent water, based on the weight of enzyme plus its hydrating water molecules. The "essentially dry" product produced in accordance with the present invention is a free-flowing powder which, by all appearances, is a dry material, i.e., not sticky or clumpy or otherwise difficult to handle.

Alcohol oxidase can be purchased commercially from chemical and biological supply houses, such as, for example, Provesta Corporation, Bartlesville, Okla.

Those of skill in the art are well aware of a variety of sources from which the stabilizing agents of the present invention can be obtained. In addition, it is recognized by those of skill in the art that proteins having functional properties of the above-described stabilizing agents can be obtained from a variety of biological sources. Thus, for example, peroxidases isolated from a variety of sources are known to vary in their substrate specificity and in their specific catalytic activity. Similarly, several different hemoglobins are known to be produced even by the same animal species. It is within the contemplation of the present invention that stabilizing agents obtained from any of the various available sources of the above-mentioned group of stabilizing agents will be effective to impart a stabilizing effect on alcohol oxidase.

In accordance with the present invention, either crude or purified alcohol oxidase can be prepared in stabilized, essentially dry form by adding a stabilizing amount of at least one stabilizing agent selected from the group consisting of: catalase, peroxidase, hemoglobin, cytochrome c and myoglobin to the alcohol oxidase as a dry blend, in solution or as a suspension (containing an alcohol oxidase concentration of up to 10 mg/mL). Presently preferred stabilizing agents are peroxidase and catalase because of their excellent performance, ready availability, and relative low cost.

While those of skill in the art can readily determine suitable amounts of stabilizing agents to employ, generally in the range of about 0.01 to 1.0 mg of stabilizing agent per mg of alcohol oxidase enzyme will be employed.

If desired, where the alcohol oxidase is in the form of a solution or suspension, the aqueous medium of alcohol oxidase can be a buffered media. Many suitable buffering systems exist and are well known in the art, such as for example, phosphate buffer, HEPES buffer (N-2-hydroxyethylpiperazine-N'-2-ethanesulfonic acid), MOPS buffer (3-[N-morpholino] propanesulfonic acid), and the like. A pH in the range of about 6 to 9 is generally preferred.

In order to prepare essentially dry alcohol oxidase, the solution or suspension containing stabilizing agent and alcohol oxidase is subjected to conditions suitable for the removal of substantially all the free water, i.e., non-enzyme bound water, from the alcohol oxidase containing solution or suspension. Those of skill in the art recognize that numerous methods for the removal of water from the aqueous phase can be employed. For example, the enzyme solution or suspension can be treated at room temperature or below with a vigorous gas stream to aid water removal. Alternatively, the enzyme suspension can be warmed up to about 40° C. in the presence or absence of a gas stream. Temperatures in excess of 40° C. are also suitable so long as prolonged exposure of enzyme to such elevated temperatures is avoided to reduce the likelihood of thermal degradation of the alcohol oxidase. As yet other alternatives, the enzyme suspension can be dried by vacuum desiccation, spray drying, freeze drying and the like. Preferably, water removal is carried out by passing a flow of gas over the alcohol oxidase solution or suspension at atmospheric pressure and at a temperature of about 20° to 40° C. at a rate sufficient to produce a dried enzyme composition in a convenient period of time, e.g., in the range of about 0.3 to 18 hours. Preferably the amount of time required for drying should be held to a minimum to minimize the reduction in alcohol oxidase activity as a result of exposure to the drying conditions.

Depending on the mode of drying employed, the stabilized, essentially dry alcohol oxidase compositions of the present invention can be obtained in the form of a powder, a film, impregnated in an inert matrix, and the like.

The resulting stabilized, essentially dry alcohol oxidase compositions retain a substantial percentage of the original enzyme activity displayed by the freshly prepared enzyme.

My invention is further illustrated by the following nonlimiting examples.

EXAMPLE I

In a continuous aerobic fermentation process, methanol and an aqueous mineral salts medium in a volume ratio of about 40 to 60, respectively, were fed individually to a fermentor, innoculated with the yeast species *Pichia pastoris* NRRL Y-11430, at a rate so that methanol is the growth-limiting factor. The fermentor was a 1500-liter foam-filled fermentor with a liquid volume of about 610 liters, with automatic pH, temperature, and level control. Agitation was provided by two conventional paddle-type turbines driven at 1000 RPM. The aeration rate was about 4 volumes of air (at about 38 psig and about 25° C.) per volume of ferment in the fermentor per minute. Anhydrous ammonia was added at such rate as to maintain the pH of the fermentation mixture at about 3.5.

The aqueous mineral salts medium was prepared by mixing, with each liter of tap water, 15.86 mL 75 percent $H_3PO_4$, 9.53 g $K_2SO_4$, 7.8 g $MgSO_4.7H_2O$, 0.6 g $CaCl_2.2H_2O$, and 2.6 g 85 percent KOH. The trace mineral solution plus biotin was fed separately via the methanol stream at a rate of 10 mL per liter of methanol. The trace mineral solution plus biotin was prepared by mixing 780 mL of a trace mineral solution, 20 mL water, 200 mL methanol and 0.032 g biotin.

The trace mineral solution was prepared by mixing, for each liter of solution, 65 g $FeSO_4.7H_2O$, 20 g $ZnSO_4.7H_2O$, 3.0 g $MnSO_4.H_2O$, 6.0 g $CuSO_4.5H_2O$, 5.0 mL conc. $H_2SO_4$, and sufficient deionized water to make 1 liter of solution.

The aqueous mineral salts medium was fed at a rate of 31.5 liters per hour and the methanol at a rate of 21 liters per hour.

The fermentation was conducted at about 30° C. and about 38 psig pressure, with a retention time of 11.6 hours.

For analytical purposes, the resulting yeast cells were separated from the fermentation effluent (ferment) by centrifugation, washed by suspension in water and recentrifugation, dried overnight at 100° C., and weighed. On a dried basis, the yield of yeast cells typically was about 40.6 g per 100 g of methanol feed. The cell density typically was about 128.4 g of cells per liter of fermentor effluent. The total solids content of the ferment typically was about 134.7 g per liter, cells plus dissolved solids. A portion of the fermentor effluent was frozen and stored. In addition, a portion of the fermentor effluent was removed and adjusted to pH 7.5 with ammonium hydroxide, and was homogenized in a Bead Beater Cell Disrupter (Biospec Products) filled to 50% volume with spherical glass grinding media at 15° C. (average temperature) for a total period of 3 minutes. The beads in the cell disrupter were lead-free glass beads with a diameter of 0.3-0.5 mm. The resulting homogenate was centrifuged at 5° C. and $20,000 \times g$ for 30 minutes to yield a cell-free supernatant.

Six 130 mL portions of the supernatant were placed in cellulose acetate dialysis bags and dialyzed at 5° C. against about 8 liters of distilled water. After 18 hours, the aqueous phase of each bag was decanted. The solids remaining in the bags consisted of two types of solid. The thin upper white layer was carefully removed and discarded. The bottom solid was brown-yellow and was the alcohol oxidase.

A sample of the solid alcohol oxidase was examined by SDS gel electrophoresis and a single band was observed indicating a homogeneously pure enzyme.

This example demonstrates the process utilized for the preparation and isolation of pure alcohol oxidase employed in the stabilization studies described in Example II.

EXAMPLE II

Aqueous alcohol oxidase, an additive to be tested for stabilizing agent activity, water, and optionally buffer, were mixed in a spot plate, air-dried, subjected to an accelerated aging test, then assayed for remaining enzyme activity. Thus, 10 $\mu$L aliquots of a 35% aqueous sucrose solution of pure alcohol oxidase (prepared as described in Example I) and containing about 0.3-0.5 mg of alcohol oxidase, were placed in the depressions of a spot plate. To each depression was added 100 $\mu$L of water, optionally containing 1 mg/mL of a putative stabilizing agent and buffer. The ~110 $\mu$L of alcohol oxidase containing suspension was dried overnight by placing the spot plate on the ledge of a laboratory fume hood and allowing the vigorous flow of room air through the hood to pass over the spot plate for about 12-18 hours. The "dried" samples were then placed in a forced air oven at about 60°-70° C. for 0.5-1 hour (accelerated aging conditions) before being cooled, redissolved in water and assayed for alcohol oxidase activity.

The alcohol oxidase activity for reaction with methanol was determined by the following assay procedure (dye-peroxidase method). A dye-buffer mixture was prepared by mixing 0.1 mL of an O-dianisidine solution (1 weight % o-dianisidine in water) with 12 mL of aerated 0.1 M sodium phosphate buffer (pH 7.5). The assay mixture was prepared with 2.5 mL of the dye-buffer mixture, 50 μL of methanol, 10 μL of a peroxidase solution (1 mg of horse-radish peroxidase-Sigma, Type II), and 25 μL of the alcohol oxidase solution. The assay mixture was maintained at 25° C. in a 4×1×1 cm cuvette and the increase in absorbance by the dye at 460 nm was recorded for 2 to 4 minutes. The enzyme activity was calculated by $$\text{Activity (μmole/min/mL or Enzyme Units/mL)} = \frac{\Delta A}{\min} \times 11.5$$

wherein 11.5 is a factor based on a standard curve prepared with known aliquots of $H_2O_2$ and $\Delta A$ is the change in absorbance during the experimental interval.

The conditions and results of several tests are summarized in Table I. The activity of alcohol oxidase which was dried and aged as described above was adjusted to a normalized value of 100, with all other activities adjusted relative to this normalized value in order to reflect the amount of stabilization/destabilization imparted by the specific additive tested. To provide a basis for comparison, fresh alcohol oxidase, absent any additive and prior to drying, had a relative activity in the range of 184–190 for the two runs reported in Table I; while the alcohol oxidase relative activity after drying (again, absent any additive) was in the range of 136–143. After being subjected to the accelerated aging conditions set forth above, the relative alcohol oxidase activity for each run (Test A and B in the table was 100.

TABLE I

| Sample Tested | Relative Alcohol Oxidase Activity Test* | |
|---|---|---|
| | A | B |
| A. Control Run | | |
| Dried, aged alcohol oxidase | 100 | 100 |
| B. Comparison Runs | | |
| Ferric Ammonium citrate +AO | 126 | — |
| Ferrocene dicarboxylic acid +AO | 62 | — |
| Irone choline citrate +AO | 110 | — |
| Ferritin +AO | 80 | — |
| Potassium ferricyanide +AO | 78 | — |
| Hemocyanin +AO | 87 | 93 |
| Bovine serum albumin +AO | — | 91 |
| Tyrosinase +AO | 94 | 96 |
| Ascorbic Oxidase +AO | 87 | 72 |
| C. Invention Runs | | |
| Horseradish peroxidase +AO | 132 | 163 |
| Catalase +AO | 140 | 136 |
| Hemoglobin +AO | 0** | 113 |
| Cytochrome c +AO | 148 | 115 |
| Microperoxidase +AO | 124 | 122 |
| Myoglobin +AO | 219 | 129 |

*Test conditions:
A = Alcohol oxidase (AO), water and putative stabilizer only; relatively deep well spot plates employed suggest that drying rate was comparatively slow (compare Test B); accelerated aging conditions of 70° C. for 1 hour.
B = AO, water and putative stabilizer only; shallow well spot plates employed suggest that the drying rate was relatively rapid (compare Test A); accelerated aging conditions of 70° C. for 30 minutes.
**Assay error suspected; non-zero value should be observed regardless of the level of stabilization achieved.

The results presented in Table I demonstrate the ability of peroxidases (e.g., horseradish peroxidase and microperoxidase), catalase, hemoglobin, cytochrome c and myoglobin to improve the stability of alcohol oxidase when prepared in dry form.

The variation in results for several of the additives tested presumably results from variations in the humidity of the laboratory air drawn through the fume hood during drying, the degree to which the alcohol oxidase in the spot plate was dried prior to being subjected to the "accelerated aging conditions", and numerous other variables which were not capable of close control as a result of the manner in which the tests were run.

The examples have been provided merely to illustrate the practice of my invention and should not be read so as to limit the scope of my invention or the appended claims in any way. Reasonable variations and modifications, not departing from the spirit of my invention, are contemplated to be within the scope of patent protection desired and sought.

That which is claimed is:

1. An enzyme composition consisting essentially of
   (a) alcohol oxidase, and
   (b) a stabilizing amount of at least one stabilizing agent selected from the group consisting of: peroxidase, catalase, hemoglobin, cytochrome c and myoglobin.

2. A composition in accordance with claim 1 wherein said alcohol oxidase is isolated from a strain of the genus Pichia.

3. A composition in accordance with claim 2 wherein said alcohol oxidase is isolated from a strain of the species *Pichia pastoris*.

4. A composition in accordance with claim 1 wherein said stabilizing amount is in the range of 0.01 to 1.0 mg of stabilizing agent per mg of alcohol oxidase enzyme.

5. A composition in accordance with claim 1 wherein said peroxidase is horseradish peroxidase.

6. A composition in accordance with claim 1 wherein said stabilizing agent is catalase.

7. A composition in accordance with claim 1 wherein said composition exists as an aqueous solution or suspension.

8. A composition in accordance with claim 1 wherein said composition exists in essentially dry form.

9. A method for preparing stabilized, essentially dry alcohol oxidase which comprises:
   (a) dissolving or suspending up to 100 mg/mL of alcohol oxidase in aqueous medium in the presence of a stabilizing amount of at least one stabilizing agent selected from the group consisting of: peroxidase, catalase, hemoglobin, cytochrome c and myoglobin; and then
   (b) removing substantially all of the water from the combination prepared as described in step (a) under conditions suitable to produce essentially dry alcohol oxidase.

10. A method in accordance with claim 9 wherein said alcohol oxidase is isolated from a strain of the genus Pichia.

11. A method in accordance with claim 10 wherein said alcohol oxidase is derived from a strain of the species *Pichia pastoris*.

12. A method in accordance with claim 9 wherein said stabilizing amount is in the range of 0.01 to 1.0 mg of stabilizing agent per mg of alcohol oxidase enzyme.

13. A method in accordance with claim 9 wherein said peroxidase is horseradish peroxidase.

14. A method in accordance with claim 9 wherein said stabilizing agent is catalase.

15. A method in accordance with claim 9 wherein said aqueous medium comprises a buffer in the pH range of about 6 to 9.

16. A method in accordance with claim 9 wherein step (b) is carried out at atmospheric pressure, a temperature in the range of about 20° to 40° C., and with a gas flow passing over the alcohol oxidase solution or suspension at a rate sufficient to cause removal of substantially all of the water from the alcohol oxidase solution or suspension.

* * * * *